United States Patent [19]

Patel

[11] Patent Number: 5,358,708
[45] Date of Patent: Oct. 25, 1994

[54] STABILIZATION OF PROTEIN FORMULATIONS

[75] Inventor: Suman T. Patel, Neshanic Station, N.J.

[73] Assignee: Schering Corporation, Kenilworth, N.J.

[21] Appl. No.: 11,431

[22] Filed: Jan. 29, 1993

[51] Int. Cl.$^5$ .............................................. A61K 45/05
[52] U.S. Cl. .................. 424/85.1; 424/85.2; 530/351
[58] Field of Search .............. 530/351; 424/85.1, 85.2, 424/85.4, 85.5, 85.6, 85.7

[56] References Cited

U.S. PATENT DOCUMENTS

| | | | |
|---|---|---|---|
| 3,950,513 | 4/1976 | Jensen | 424/94 |
| 4,440,679 | 4/1984 | Fernandes et al. | 530/350 |
| 4,496,537 | 1/1985 | Kwan | 424/85 |
| 4,645,830 | 2/1987 | Yasushi et al. | 530/351 |
| 4,675,183 | 6/1987 | Kato et al. | 424/85.4 |
| 4,777,043 | 10/1988 | Bennett et al. | 424/94.64 |
| 4,806,524 | 2/1989 | Kawaguchi et al. | 514/8 |
| 4,824,674 | 4/1989 | Becker et al. | 424/85.7 |
| 4,855,134 | 8/1989 | Yamahira et al. | 424/85.7 |
| 4,895,716 | 1/1990 | Goldstein et al. | 424/85.5 |
| 4,983,386 | 1/1991 | Kamishita et al. | 424/85.4 |
| 4,992,419 | 2/1991 | Woog et al. | 514/12 X |

FOREIGN PATENT DOCUMENTS

| | | |
|---|---|---|
| 0082481 | 6/1983 | European Pat. Off. |
| 0163111 | 4/1985 | European Pat. Off. |
| 9181223 | 6/1984 | Japan |
| 9181224 | 10/1984 | Japan |
| 9215614 | 9/1992 | World Int. Prop. O. |

OTHER PUBLICATIONS

R. L. Levine, "Oxidative Modification of Glutamine Synthetase," in *Journal of Biological Chemistry*, vol. 258, pp. 11828–11833 (1983).

A. Amici, R. L. Levine, L. Tsai & E. R. Stadtman, "Conversion of Amino Acid Residues in Proteins and Amino Acid Polymers to Carbonyl Derivatives by Metal-Catalyzed Oxidation Reactions," in *Journal of Biological Chemistry*, vol. 264, pp. 3341–3346 (1989).

Y-C. J. Wang & M. A. Hanson, "Parenteral Formulations of Proteins and Peptides: Stability and Stabilizers," in *Journal of Parenteral Science & Technology*, vol. 42, Supplement 1988, pp. 53–526.

Derwent Abstract 84–292020/47 of Japanese Patent Application 59/181,224.

Derwent Abstract 22858 E/12 of Japanese Patent Application 57/26,587.

*Primary Examiner*—Michael G. Wityshyn
*Assistant Examiner*—C. Sayala
*Attorney, Agent, or Firm*—Eric S. Dicker; John J. Maitner; Robert A. Franks

[57] ABSTRACT

Aqueous formulations of an interferon, a granulocyte-macrophage colony-stimulating factor or an interleukin are made to have extended storage lifetimes by incorporating methionine, histidine or mixtures thereof.

12 Claims, 3 Drawing Sheets

STABILIZATION OF PROTEIN FORMULATIONS

This invention relates to methods for the stabilization against decomposition of aqueous formulations containing proteins and, more particularly, to increasing the storage lifetime of formulations containing an interferon, a granulocyte-macrophage colony-stimulating factor or an interleukin.

Considerable study has been made of the decomposition mechanisms of proteins, reflecting both academic and clinical interests. A paper was published by R. L. Levine ("Oxidative Modification of Glutamine Synthetase, II. Characterization of the Ascorbate Model System," in *Journal of Biological Chemistry*, Vol. 258, No. 19, Oct. 10, 1983, pp. 11828–11833) to report studies of glutamine synthetase degradation in a system containing oxygen, ascorbate and trace metal. A table in this paper shows results from testing 24 amino acids and sulfhydryl compounds as stabilizers; only cysteine and histidine showed significant activity in preventing loss of activity for the enzyme, some of the compounds tested actually stimulating the inactivation reaction. It is also stated that the inactivation of the enzyme creatine kinase by ascorbate is stimulated by histidine. Thus, the art has recognized that different proteins exhibit widely varying inactivation responses.

U.S. Pat. No. 4,496,537 to Kwan describes the enhancement of storage stability of lyophilized alpha-type interferon formulations, by incorporating glycine or alanine prior to lyophilization. Formulations can be stored without loss of activity for more than six months at 20° C. before reconstitution with water.

Kawaguchi et al., in U.S. Pat. No. 4,806,524 describe the stabilization of freeze-dried or aqueous erythropoietin formulations against decomposition, by adding one or more of polyethylene glycol, proteins, sugars, amino acids, inorganic salts, organic salts and sulfur-containing reducing agents.

U.S. Pat. No. 4,777,043 to Bennett et al. relates the increase in solubility and stability obtained when human tissue plasminogen activator formulations are made to contain arginine, as the protonated cation "argininium ion."

In U.S. Pat. No. 4,645,830 to Yasushi et al., interleukin-2 was stabilized against loss of activity during freezing, lyophilization or storage, by formulating with human serum albumin, a reducing compound or both, and adjusting the pH within the range of 3 to 6. The formulation may also contain an amino acid, particularly glycine, a monosaccharide, and/or a sugar alcohol.

According to U.S. Pat. No. 3,950,513 to Jensen, the solubility and stability of plasmin solutions for parenteral administration are enhanced by the addition of physiologically non-toxic amino acids.

Y-C. J. Wang and M. A. Hanson, in a literature review entitled "Parenteral Formulations of Proteins and Peptides: Stability and Stabilizers," Technical Report No. 10, *Journal of Parenteral Science and Technology*, Vol. 42, Supplement 1988, discuss at pages S12 and S13 the use of amino acids to stabilize parenteral formulations of proteins and peptides.

An abstract of Japanese Patent Application 57-26587 describes the stabilization of ascorbic acid oxidase by adding one or more of arginine, lysine, histidine and borates.

An abstract of Japanese Patent Application 59-181224 discloses an enhanced stability for interferons having added an amino acid and, optionally, human serum albumin before freeze drying.

Pharmaceutical formulations of interferons, granulocyte-macrophage colony-stimulating factors and interleukins are normally available as lyophilized powders, accompanied by sterile aqueous media for reconstitution. After reconstitution, the formulations typically have short useful storage lives, even when stored at low temperatures (e.g., 5° C.). Thus, it is desirable to provide aqueous formulations having enhanced storage lives under refrigeration and a moderate useful life at normal room temperatures, and to avoid the inconvenience and potential for errors from the reconstitution procedure.

SUMMARY OF THE INVENTION

The present invention is a method for stabilizing aqueous formulations of interferon, granulocyte-macrophage colony-stimulating factor or interleukin against changes in potency during storage, comprising adding to the formulations a stabilizing amount of histidine, methionine or mixtures thereof.

DETAILED DESCRIPTION OF THE INVENTION

Figure 1:
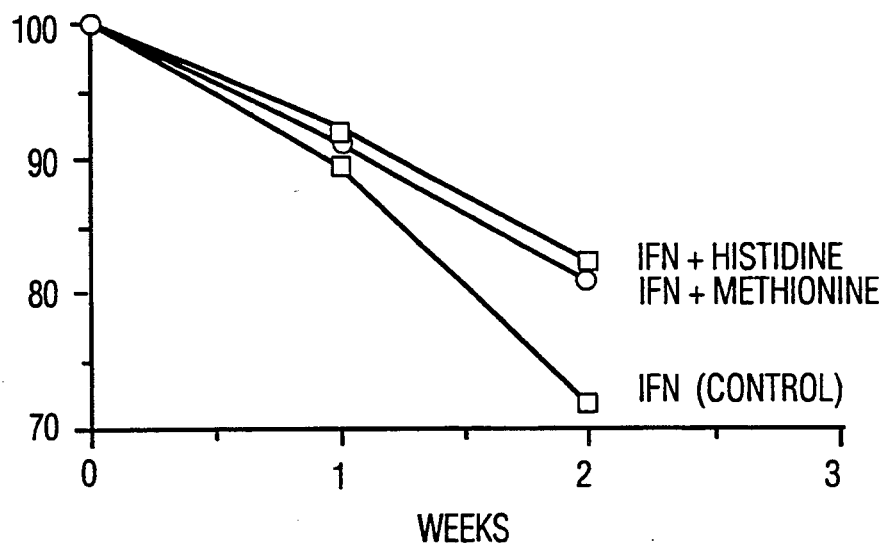
FIG. 1 is a graphical presentation of the results of an experiment to show the stabilization of interferon-$\alpha$-2$b$ with methionine and histidine.

Proteins which can be stabilized by the present invention include interferons. As used herein, "interferon" (sometimes abbreviated "IFN") refers to any of the family of proteins produced in the human body (including related proteins produced by recombinant DNA technology), which confer resistance to viral infection, affect the proliferation of cells and modulate the response of the immune system. Three major human interferons have been identified, each possessing different antigenic and physicochemical properties and being derived from different cellular sources, in response to different inducers: interferon-$\alpha$, interferon-$\beta$ and interferon-$\gamma$.

The present invention is well suited for use with aqueous formulations of interferon-$\alpha$, of which there are at least 24 subspecies. Of particular preference is the interferon-$\alpha$-2, having two forms with current therapeutic importance called "a" and "b." Interferon-$\alpha$-2$b$ has a sequence of 165 amino acids and a formula of $C_{860}H_{1353}N_{229}O_{255}S_9$. Interferon-$\alpha$-2$a$ has the same formula, except for having only 227 nitrogen atoms. The interferon-$\alpha$ proteins are isolated from natural sources (human peripheral blood lymphocytes, human lymphoblastoid cell lines, and others) or are cloned and expressed using recombinant DNA techniques and organisms such as *E. coli*.

Granulocyte-macrophage colony-stimulating factor (frequently abbreviated "GM-CSF") supports growth and development of granulocytes, and is used therapeutically to treat neutrophil deficiency and for rehabilitative therapy after treatment of tumors by radiation or chemotherapy. Non-recombinant human GM-CSF can be purified from culture media, and GM-CSF also has been produced by recombinant DNA techniques, using organisms such as yeasts and *E. coli*. Similar biological activity is seen for many variants of GM-CSF (having substitutions, deletions and/or insertions of amino acids), and the use of all sequences having therapeutic uses is contemplated for the present invention.

Particularly preferred GM-CSF for the present invention is that expressed by an *E. coli* bacterium (MC1061) carrying the pcD-human-GM-CSF plasmid, which bacterium has been deposited with the American Type Culture Collection, Rockville, Md., U.S.A. under accession number 39923.

Interleukins which are useful for the present invention include all of the family of interleukins having immune system activity and therapeutic uses. These include, without limitation, the members of the family known by the abbreviations "IL-1," "IL-2," "IL-3", "IL-4" and "IL-10." The invention is particularly applicable to mammalian interleukin-4, as described in U.S. Pat. No. 5,017,691 to Lee et al. which is incorporated herein by this reference. It should be noted that considerable substitution, deletion and addition of amino acids can be done, without affecting biological activity of the protein, and all active molecules are included within the term "interleukin." Thus, for example, the term "IL-4" will include the specific interleukin-4 proteins which are naturally expressed by cells of a mammal, plus all related proteins produced by recombinant DNA technology and having IL-4 activity.

Aqueous pharmaceutical preparations of each of the previously described proteins are noted for their storage instability. While the exact mechanism is not known with any certainty, it is believed that most protein degradation in aqueous media is the result of oxidation reactions occurring with pendant groups on amino acids in the protein structure; in any event, the present invention is not dependent upon any particular theory of operation. The pharmaceuticals are generally supplied only in the form of lyophilizates, together with aqueous media for reconstitution. Frequently, the packaging includes only a unit dose, which is immediately administered after reconstitution. In the event that reconstituted formulations are to be stored, refrigeration at temperatures barely above freezing is required and will provide only a limited storage life, e.g., usually no more than one month. This need for reconstitution obviously is a matter of inconvenience and adds both to the expense of treatment with the proteins and the possibility of incorrect dosing.

It has now been found that aqueous formulations of interferons, granulocyte-macrophage colony-stimulating factors and interleukins can be made to have extended storage lifetimes, when effective amounts of the amino acids methionine, histidine or mixtures thereof are incorporated into the formulations. In some instances, useful storage lifetimes can be obtained without the need for careful refrigeration. In other instances, although refrigeration remains advisable, the storage lifetime is extended and aqueous formulations can be made available to avoid entirely the inconvenience of reconstitution.

For purposes of the present invention, an effective amount of methionine, histidine or mixtures thereof is that amount which provides an aqueous formulation of a protein with the required storage lifetime, such storage being under conditions specified by a particular user. It should be apparent that different proteins will become inactivated during storage at different rates and under different conditions, due to chemical differences between the proteins. The presence of trace impurities in the formulations (such as metal ions) may catalyze decomposition reactions. Also, the storage-prolonging effects of methionine and histidine are not equivalent with the different proteins and, of course, mixtures of the amino acids will exhibit different effects as the ratio is varied, the identity of the protein is changed and/or the concentrations are altered.

In general, it is usually desired to obtain a concentration ratio of amino acid to protein at least about 10 to 1. More preferred are ratios at least about 50 to 1. Still more highly preferred are ratios at least about 100 to 1. The exact ratio required for a particular combination of protein, formulation components, amino acid or mixture and prescribed storage conditions can be determined by simple experimentation, using the usual analytical techniques for protein activity or concentration over the desired storage lifetime.

The invention is further described by the following examples, which are not intended to be limiting, the scope of the invention being defined solely by the appended claims.

EXAMPLE 1

An aliquot of an aqueous solution of recombinant human interferon-$\alpha$-2$b$ is diluted with a 20 mM citrate-phosphate buffer, pH 6.9, to prepare 10 ml of a solution containing 150 $\mu$g of interferon. Similar solutions also containing 20 mg of either methionine or histidine are prepared. The solutions are stored for two weeks at 40° C. Samples of the solutions are analyzed upon preparation and again at weekly intervals by reverse phase high performance liquid chromatography, giving results as shown in FIG. 1.

Both methionine and histidine are effective in extending the storage life of interferon-$\alpha$-2$b$.

EXAMPLE 2

Figure 2:
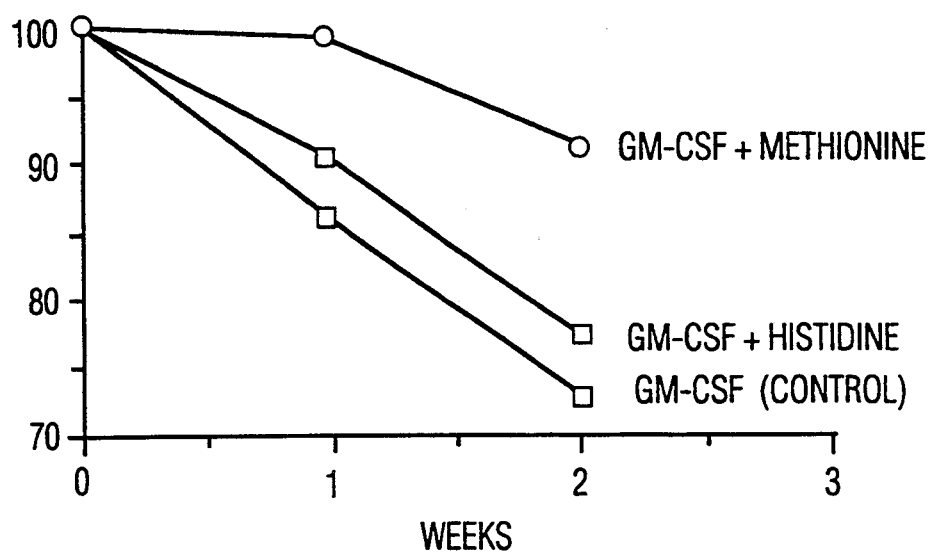
FIG. 2 is a graphical presentation of the results of an experiment to show the stabilization of granulocyte-macrophage colony-stimulating factor with methionine and histidine.

An aliquot of aqueous solution of recombinant human granulocyte-macrophage colony-stimulating factor is diluted as in the preceding example, to prepare 10 ml of a solution containing 500 $\mu$g of GM-CSF. Similar solutions are prepared to also contain 20 mg of either methionine or histidine. The solutions are stored at 40° C. for two weeks, and analyzed by reverse phase high performance liquid chromatography at weekly intervals, giving results as shown in FIG. 2.

Both methionine and histidine extend the storage lifetime of GM-CSF, but methionine is somewhat more effective for high-temperature storage under the conditions of this test.

Figure 3A:
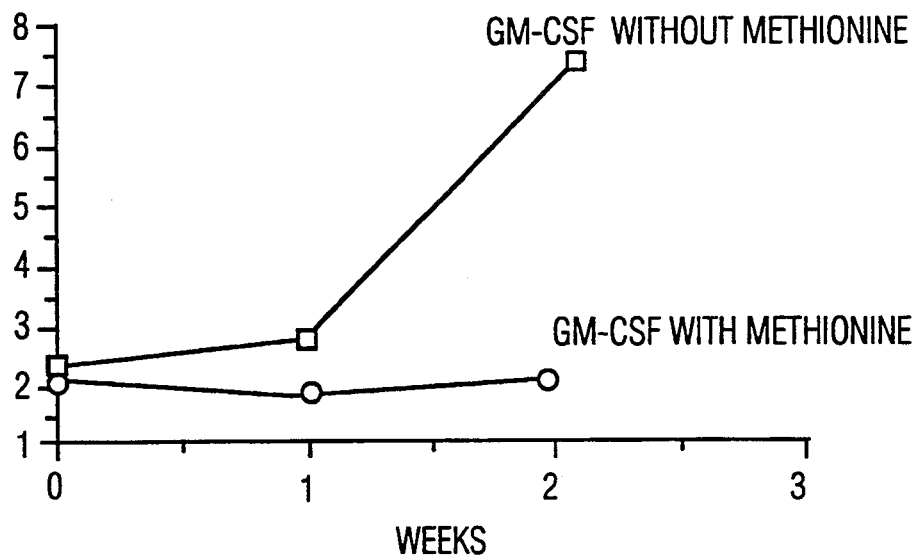
FIGS. 3$a$ and 3$b$ show the results of an experiment to determine the effect of methionine on the formation of granulocyte-macrophage colony-stimulating factor degradation products.
Figure 3B:
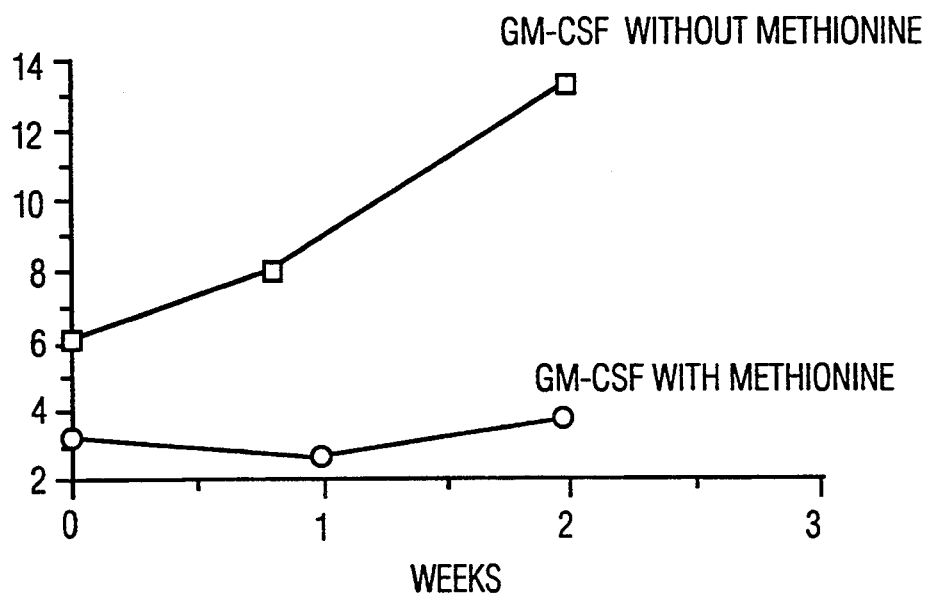

FIGS. 3$a$ and 3$b$ show the effect of methionine on the formation of two different unidentified degradation products of GM-CSF during the test. The vertical axis of these figures is graduated in units which are percentage of the total GM-CSF amount eluted from the liquid chromatograph column.

EXAMPLE 3

Figure 4:
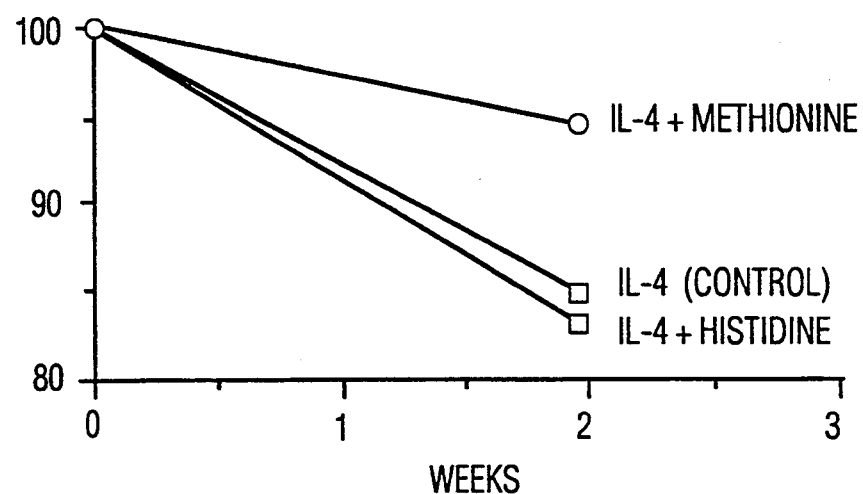
FIG. 4 is a graphical presentation of the results of an experiment to show the stabilization of interleukin-4 with methionine and histidine.

An aliquot of an aqueous solution of recombinant human interleukin-4 is diluted with a 10 mM aqueous sodium citrate buffer, pH 4.5, to prepare 10 ml of a solution containing 500 μg of IL-4. Similar solutions are prepared also containing 20 mg of either methionine or histidine. Each solution is stored at 40° C. for two weeks, with weekly analyses for IL-4 content by reverse phase high performance liquid chromatography. The results are as shown in FIG. 4.

Methionine is effective in extending the storage lifetime of IL-4 solutions at high temperatures, but histidine is considerably less effective under the conditions of this test.

EXAMPLE 4

Formulations containing 50 μg/ml of GM-CSF are prepared in the buffer of Example 1. One of the formulations contains 2 mg/ml of glycine, and another contains 2 mg/ml of methionine. Aliquots of each formulation and a control formulation which does not contain added amino acid are stored for one-half month at −80° C., while other aliquots are stored for similar periods at 40° C. All aliquots are analyzed after storage for GM-CSF and degradation products content, by reverse phase high performance liquid chromatography. The results given below show the percentage of GM-CSF which undergoes degradation in each aliquot, and indicate that glycine is not an effective stabilizer of the GM-CSF protein for storage at elevated temperatures.

| Amino Acid | −80° C. Degradation | 40° C. Degradation |
|---|---|---|
| None | 1.3 | 4.8 |
| Glycine | 1.3 | 5.1 |
| Methionine | 1.3 | 3.1 |

The invention has been described with respect to certain specific embodiments, and further modifications and embodiments will become apparent to those skilled in the art. All such modifications and embodiments are included within the scope of the appended claims.

What is claimed is:

1. A method for increasing the storage stability of an aqueous formulation containing a protein component selected from the group consisting of a granulocyte-macrophage colony-stimulating factor and an interleukin, the method comprising adding a stabilizing amount of methionine, histidine or mixtures thereof to the formulation.

2. The method of claim 1, wherein the concentration ratio of methionine, histidine or mixtures thereof to the protein component is at least about 10 to 1.

3. The method of claim 1, wherein the concentration ratio of methionine, histidine or mixtures thereof to the protein component is at least about 50 to 1.

4. The method of claim 1, wherein the concentration ratio of methionine, histidine or mixtures thereof to the protein component is at least about 100 to 1.

5. The method of claim 1, wherein methionine is added to the formulation.

6. An aqueous formulation containing a protein selected from the group consisting of a granulocyte-macrophage colony-stimulating factor and an interleukin, also containing a storage stability-enhancing amount of methionine, histidine or mixtures thereof.

7. The formulation of claim 6, wherein the methionine, histidine or mixtures thereof are present in concentrations which are at least about 10 times that of the protein.

8. The formulation of claim 6, wherein the protein is a granulocyte-macrophage colony-stimulating factor.

9. The formulation of claim 8, wherein the stability is enhanced by methionine.

10. The formulation of claim 8, wherein the stability is enhanced by histidine.

11. The formulation of claim 6, wherein the protein is an interleukin.

12. The formulation of claim 11, wherein the stability is enhanced by methionine.

* * * * *